United States Patent
Nicol et al.

(10) Patent No.: US 8,809,697 B2
(45) Date of Patent: Aug. 19, 2014

(54) PASSIVE COOLING AND EMI SHIELDING SYSTEM

(75) Inventors: David H. Nicol, Del Mar, CA (US); Michael Dugan Joyce, Chula Vista, CA (US); Brendan Burgess, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 551 days.

(21) Appl. No.: 13/101,881

(22) Filed: May 5, 2011

(65) Prior Publication Data

US 2012/0281360 A1    Nov. 8, 2012

(51) Int. Cl.
     *H05K 9/00*            (2006.01)
     *H05K 7/20*            (2006.01)

(52) U.S. Cl.
USPC ........... 174/383; 361/690; 361/692; 361/709; 361/800; 361/816; 361/818; 361/702; 454/184; 174/377; 174/384; 174/385; 174/548

(58) Field of Classification Search
USPC ............... 361/679.46–679.54, 688–723, 800, 361/816, 818; 454/184; 174/377, 383–385, 174/547–548
See application file for complete search history.

(56) References Cited

U.S. PATENT DOCUMENTS

| | | | | |
|---|---|---|---|---|
| 3,544,751 | A | * | 12/1970 | Valles ........................... 219/741 |
| 4,241,380 | A | | 12/1980 | Lehmann et al. |
| 4,771,365 | A | | 9/1988 | Cichocki et al. |
| 4,953,058 | A | | 8/1990 | Harris |
| 5,030,793 | A | * | 7/1991 | McCarthy ..................... 174/383 |
| 6,088,223 | A | * | 7/2000 | Diemunsch ................... 361/690 |
| 6,384,325 | B1 | * | 5/2002 | Chastain et al. .............. 174/383 |
| 6,493,227 | B2 | | 12/2002 | Nielsen et al. |
| 6,577,504 | B1 | | 6/2003 | Lofland et al. |
| 6,867,985 | B2 | * | 3/2005 | Westerinen et al. .......... 361/818 |
| 7,265,984 | B2 | * | 9/2007 | Numata ........................ 361/719 |
| 7,742,298 | B2 | | 6/2010 | Kunz |
| 7,889,503 | B2 | * | 2/2011 | Nagareda et al. ............. 361/719 |
| 2007/0128946 | A1 | * | 6/2007 | Hisamatsu et al. ........... 439/638 |
| 2009/0273904 | A1 | * | 11/2009 | Chung et al. ................. 361/700 |

FOREIGN PATENT DOCUMENTS

JP           3070968 U9     6/2000

OTHER PUBLICATIONS

International Search Report and Written Opinion for PCT/US2012/034725, mailed Nov. 14, 2012.

* cited by examiner

*Primary Examiner* — Zachary M Pape
(74) *Attorney, Agent, or Firm* — McDermott Will & Emery LLP (57) ABSTRACT

An electronics enclosure is disclosed that provides passive cooling of electronic components while reducing electromagnetic interference (EMI) emissions. The electronics enclosure includes an electronics assembly with at least one electronic component and a heat sink coupled to the electronics assembly. The heat sink has a base portion configured to thermally couple to the at least one electronic component when the heat sink is coupled to the electronic assembly. The electronics enclosure also includes a conductive enclosure forming an enclosed volume around the electronics assembly. The enclosure has a first opening configured to fit around the heat sink and at least one second opening. All non-conductive passages from the volume to the external environment have at least one cross-sectional opening having a continuous conductive perimeter with a maximum linear length within the opening of less than one quarter wavelength of a determined maximum shielding frequency.

19 Claims, 8 Drawing Sheets

PASSIVE COOLING AND EMI SHIELDING SYSTEM

BACKGROUND

1. Field

The present disclosure generally relates to systems and methods of cooling electrical components and, in particular, allowing passive cooling while also providing ElectroMagnetic Interference (EMI) shielding.

2. Description of the Related Art

Hospitals have a need to provide secure storage for certain medications, such as narcotics and controlled substances, while still making the medications available to care givers. One method of providing this secure storage is the use of Automatic Dispensing Machines (ADMs), which typically contain a microprocessor that is functionally connected to the hospital data systems and secure drawers and compartments containing the medications. The software of each ADM is normally configured to allow access to the medications only after certain requirements are met, such as verification that the individual requesting the medication is authorized to do so. The ADMs should be continuously operational as hospitals must provide care to their patients 24 hours a day.

Computer processors and motherboards are known to emit electromagnetic radiation across a wide frequency band due to the high frequency digital signals conducted through the circuits of the processor and on the board. To meet regulatory requirements that limit the amount of electromagnetic energy that can be radiated from electronic devices, processors are frequently mounted inside conductive enclosures. However, placing the processor and motherboard inside a sealed conductive shell has the effect of limiting the amount of cooling air that can enter and leave the enclosure, and therefore a fan is often used to force air through the enclosure to cool the internal electronics, as the processor will overheat without sufficient cooling and shut itself down to avoid permanent damage. These fans are typically considered to be noisy. Also, since the functioning of the fan is critical to the operation of the processor and therefore the ADM, the fan is a potential source of downtime of the equipment.

SUMMARY

There is a need to improve the operation of an ADM by providing sufficient cooling to the electronics through passive cooling, i.e. by natural air convection without the use of fans to blow air over the electronics, and still providing EMI shielding around the motherboard and processor to meet regulatory requirements.

The disclosed system provides passive cooling of electronics and EMI shielding of the same electronics. In the system, a heat sink is located at one edge of the electronics and designed to form a portion of the EMI shielding, with the shielding configured to form a chimney around the heat sink whereby air that has been warmed by the heat sink rises through the chimney and pulls cool air through the heat sink into the chimney. The result is a cooling and shielding system that cools electronics without the use of fans, thereby reducing the noise, cost, and reliability issues associated with cooling fans, while maintaining EMI shielding around the electronics.

In one embodiment, an electronics enclosure for providing passive cooling of electronic components while reducing electromagnetic interference (EMI) emissions is disclosed. The electronics enclosure includes an electronics assembly comprising at least one electronic component and a heat sink coupled to the electronics assembly. The heat sink has a base portion configured to thermally couple to the at least one electronic component when the heat sink is coupled to the electronic assembly. The electronics enclosure also includes a conductive enclosure forming an enclosed volume around the electronics assembly. The enclosure has a first opening configured to fit around the heat sink and at least one second opening. All non-conductive passages from the volume to the external environment have at least one cross-sectional opening having a continuous conductive perimeter with a maximum linear length within the opening of less than one quarter wavelength of a determined maximum shielding frequency.

In another embodiment, an electronics enclosure for providing passive cooling of electronic components while reducing EMI emissions is provided. The electronics enclosure includes an electronics assembly with a planar substrate having a leading edge and a trailing edge and at least one electronic component coupled to the substrate proximate to the leading edge. The electronics assembly also includes a heat sink coupled to the electronic assembly proximate to the leading edge of the substrate. The heat sink has a base portion, at least one heat pipe thermally coupled to the base portion, at least one thermal block thermally coupled to the base portion and configured to thermally couple to the at least one electronic component when the heat sink is coupled to the electronic assembly, and a plurality of fins thermally coupled to the base portion. The electronics enclosure also includes a conductive enclosure forming an enclosed volume around the electronics assembly, the enclosure comprising a first opening configured to fit around the heat sink and at least one second opening. All non-conductive passages from the volume to the external environment have at least one cross-sectional opening having a continuous conductive perimeter with a maximum linear length within the opening of less than one quarter wavelength of a determined maximum shielding frequency.

A method of passively cooling electronics while reducing conducted and radiated EMI emissions from the electronics is disclosed. The method includes the step of attaching a heat sink with a base portion to an electronics assembly having at least one electronic component that requires cooling and an interface connector having at least one contact with an interface impedance, the interface connector configured to mate and match impedances with a docking connector having at least one contact with an interface impedance thereby reducing the EMI radiated from conductors connected to the contacts of the docking connector, such that the base portion is thermally coupled to the at least one electronic component. The method includes the step of attaching a conductive enclosure to the electronics assembly so as to form an enclosed volume around the electronics assembly with a first opening fitted around the heat sink and at least one second opening, wherein all non-conductive passages from the enclosed volume to the external environment have at least one cross-sectional opening with a continuous conductive perimeter with a maximum linear length within the opening of less than one quarter wavelength of a determined maximum shielding frequency thereby reducing the EMI radiated through non-conductive passages in the conductive enclosure.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The following description discloses embodiments of an electronics enclosure that provides for passive cooling of the enclosed electronics while providing EMI shielding of the electronics to meet regulatory requirements on electromagnetic emissions. In certain embodiments, a finned heat sink is thermally coupled to the electronic components to be cooled on an electronics assembly. A conductive enclosure fits around the electronics with an opening fitted around the heat sink and a second opening preferably on the opposite side of the enclosure. The fins are configured such that the gap between the fins is large enough to allow sufficient air flow to provide passive cooling while substantially blocking electromagnetic waves up to a maximum shielding frequency. This avoids the need to have a perforated portion of the conductive enclosure covering the fins and in the air path, which would add flow resistance and decrease the cooling performance.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The method and system disclosed herein are presented in terms of an enclosure of a motherboard with an attached microprocessor as part of a computer system such as used in an ADM. It will be obvious to those of ordinary skill in the art that this same configuration and method can be utilized in a variety of applications enclosing a range of electronic assemblies that require both EMI shielding and cooling. Nothing in this disclosure should be interpreted, unless specifically stated as such, to limit the application of any method or system disclosed herein to a medical environment or to the dispensing of medications.

Electromagnetic radiation emitted by electronics is controlled by various regulatory agencies in countries around the world. In the United States, these regulations are currently embodied in the Code of Federal Regulations, Title 47, Part 15 (47 CFR 15) and administered by the Federal Communications Commission (FCC). For "unintentional radiators with a digital device", which generally includes computers and products that include microprocessors, the FCC has established maximum levels of emitted radiation over a ranges of frequencies having an upper frequency of 40 GHz if the device operates at a frequency above 1 GHz. Different levels of standards are provided for different environments. The Class B standard applies to equipment marketed for use in the home, even if it could be used elsewhere. Home users are likely to be annoyed by interference to TV and radio reception. Class A is a looser standard for equipment intended only for business, industrial and commercial settings. Some manufacturers design their products to comply with Class B requirements even when the products are intended for business environments.

In the medical field, automating compliance with various safety and regulatory standards has been recognized as saving labor on the part of the clinician staff as well as increasing the compliance rate, thereby increasing patient safety. To accomplish this automation, some medical devices contain microprocessors and peripheral devices of the sort used in personal computers (PCs), including Liquid Crystal Displays (LCDs) and hard drives, as well as other specialized and custom hardware devices. For example, an ADM such as the Pyxis® Medstation® 4000 contains a microprocessor that communicates with the hospital data systems and a user interface that includes an LCD display with a touchscreen.

Figure 1:
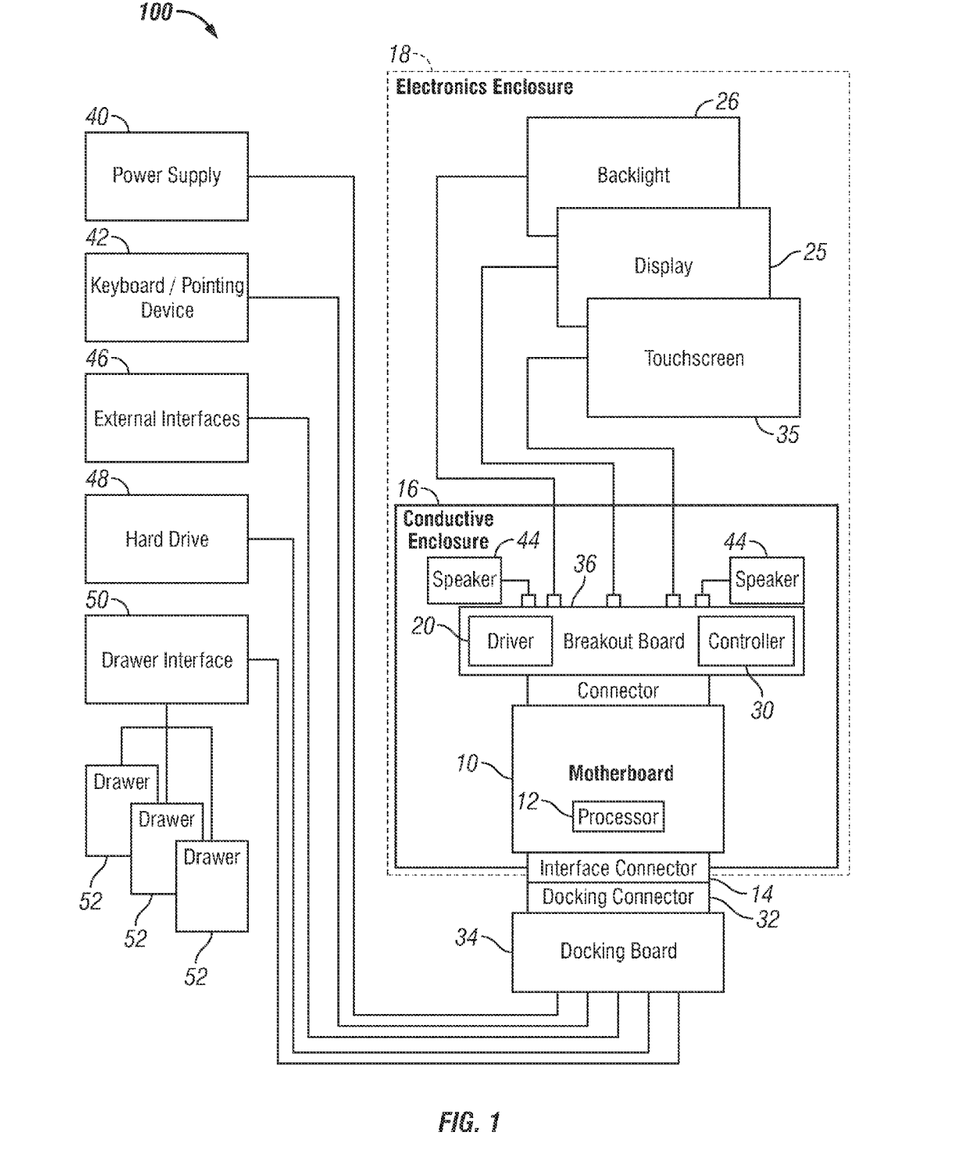
FIG. 1 is a block diagram of an embodiment of an electronics enclosure according to certain aspects of this disclosure.

FIG. 1 is a block diagram of an embodiment of an electronics enclosure 18 according to certain aspects of this disclosure. The computer system 100 includes a motherboard 10 with a microprocessor 12 and at least one interface connector 14. The processor 12 and other components (not shown) on the motherboard 10 communicate with external devices through the interface connector 14 that, in this embodiment, mates with a docking connector 32 and a docking board 34 that is then connected to the individual external devices. The external devices may include a power supply 40, a keyboard 42, speakers 44, and an external interface module 46 for communication linkages such as Ethernet, Bluetooth®, and other wired and wireless communication systems. The motherboard 10 may also connect to a hard drive 48 or other non-transient storage device such as a flash memory, and specialized devices such as a drawer interface 50 that controls one or more drawer electronics 52.

The electronics enclosure 18 includes a conductive enclosure 16 as well as a display 25 and its associated backlight 26 and a touchscreen 35. The conductive enclosure 16, in this embodiment, encloses the motherboard 10, a breakout board 36 that includes a display driver 20 and a touchscreen controller 30, and a pair of speakers 44. In certain embodiments, other devices such as hard drive 48 are also included inside the conductive enclosure 16. In certain embodiments, the motherboard 10 and microprocessor 12 are not contained in the conductive enclosure.

Figure 2A:
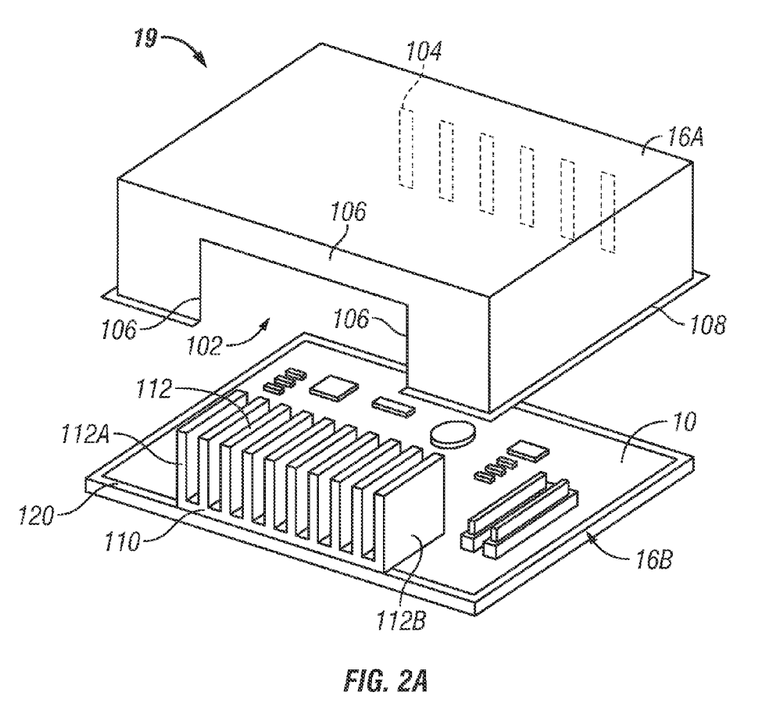
FIGS. 2A and 2B are perspective views of an electronics assembly according to certain aspects of this disclosure.
Figure 2B:
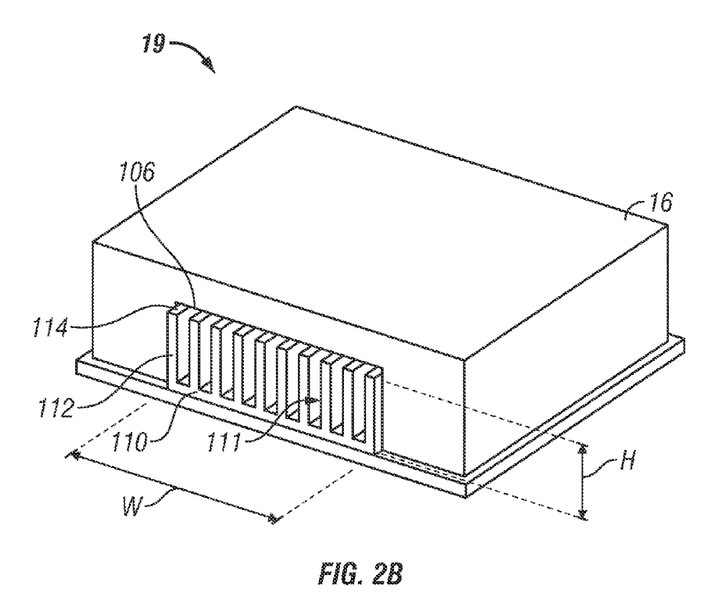

FIGS. 2A and 2B are perspective views of an electronics assembly 19 according to certain aspects of this disclosure. FIG. 2A shows a motherboard 10 that has a conductive surface 16B (referenced but not visible in this view) on the underside of the motherboard 10 that is electrically connected to a conductive strip 120 around the periphery of the upper surface of the motherboard 10. In certain embodiments, the conductive surface 16B is a separate conductive element (not shown) and the conductive strip 120 is provided directly by the conductive element and not a part of the motherboard 10. A heat sink 110 that includes a plurality of fins 112 is coupled to the motherboard 10 along one edge of the motherboard 10. A conductive cover 16A is shown above the motherboard 10. The conductive cover 16A has a first opening 102 on the side over the heat sink 110, the first opening 102 having an edge 106 around the first opening 102. The conductive cover 16A also has at least one second opening 104. The embodiment shown in FIG. 2A has six second openings 104 that are located on the side opposite to the first opening 102. The conductive cover 16A also has a flange 108 around the lower perimeter that is configured to mate with the conductive strip 120 when the conductive cover 16A is coupled with the motherboard 10.

FIG. 2B shows the conductive cover 16A coupled to the motherboard 10. The conductive cover 16A and the conductive surface 16B on the underside of the motherboard 10 together form the conductive enclosure 16 of FIG. 1. The first opening 102 is positioned around the heat sink 110 such that the edge 106 is in contact with the heat sink 110 along the outside surfaces of the end fins 112A and 112B and to the top 114 of each fin 112. In certain embodiments, the edge 106 is in electrical contact with less than all of the tops 114 of the fins 112. For example, in certain embodiments the edge 106 is in electrical contact with every other fin 112. In certain embodiments, the conductive cover 16A overlaps a portion of the external faces of fins 112 such that opening 102 is smaller than the projected cross-section of the fins 112. The gaps around the heat sink 110 are discussed more fully in relation to FIGS. 5-8.

The portion of the heat sink 110 that is exposed by opening 102 forms a front plane 111. Air passing through the front plane passes over the cooling surfaces of the fins 112 and, if the fins 112 are warmer than the incoming air, heat is transferred from the fins 112 to the air. The front plane 111 of the heat sink 110 has a width W and a height H, and the edge 106 of conductive cover 16 is sealed to the heat sink 110 sufficient that the majority of the air that enters the opening 102 will, in this embodiment, pass between the fins 112. In certain embodiments, other heat transfer structures (not shown) replace the fins 112 and the air entering opening 102 will pass through those heat transfer structures. In certain embodiments, the opening 102 is smaller than the heat sink 110 and the front plane 111 is less than the physical width or height of the heat sink 110.

Figure 2C:
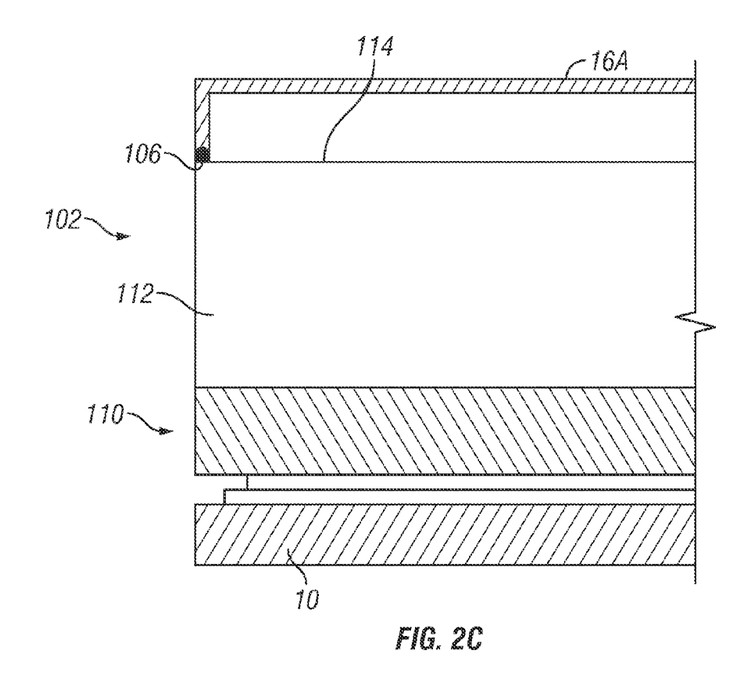
FIGS. 2C and 2D are side-view cross-sections of the opening of the electronics assembly according to certain aspects of this disclosure.
Figure 2D:
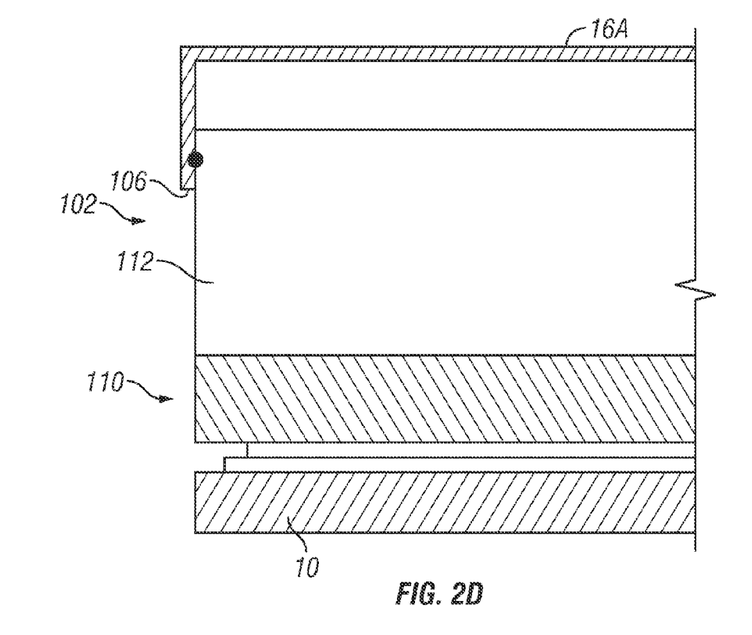

FIGS. 2C and 2D are side-view cross-sections of the opening 102 of the electronics assembly 19 according to certain aspects of this disclosure. FIGS. 2C and 2D both show the motherboard 10 with the heatsink 110 mounted in alignment with the edge of the motherboard 10, and the conductive cover 16A over the fins 112 of the heatsink 110. In FIG. 2C, the opening 102 is configured to match the profile of the fins 112 and the edge 106 of the conductive cover 15 make electrical contact with the top 114 of one or more of the fins. In FIG. 2D, it can be seen that the opening 102 is smaller than the profile of the fins 112 and the edge 106 makes electrical contact with the front face of at least one fin 112. In certain embodiments, the heat sink 110 is recessed from the edge of the motherboard 10. In certain embodiments, the edge 106 is recessed from the edge of the motherboard 10 and makes contact with the top 114 of at least one fin 112 at a point away from the front face of the fins 112.

Figures 3A, 3B:
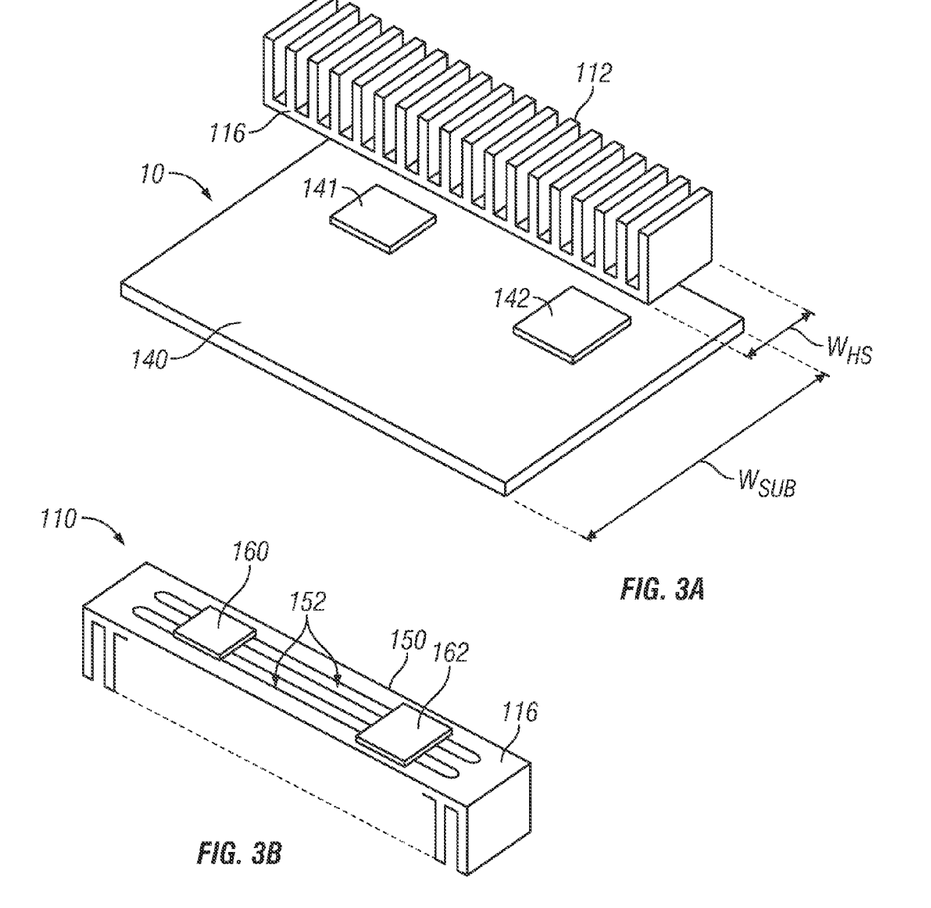
FIGS. 3A-3C are perspective views of a heat sink according to certain aspects of this disclosure.
Figure 3C:
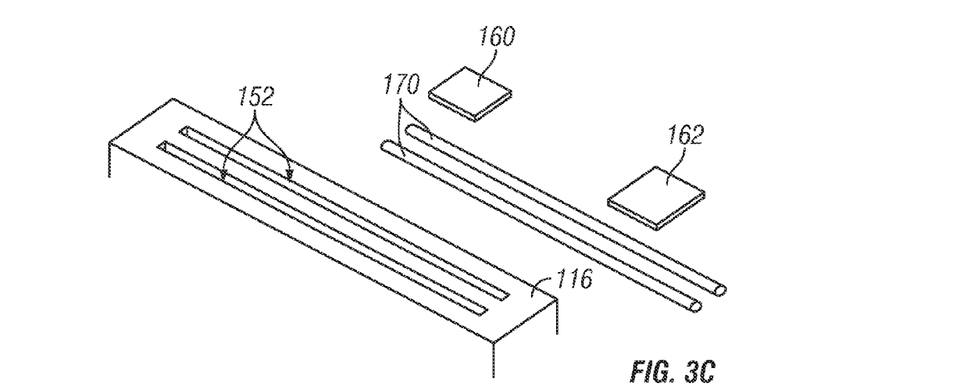

FIGS. 3A-3C are perspective views of a heat sink 110 according to certain aspects of this disclosure. FIG. 3A shows an exploded view of a heat sink 110 over a motherboard 10 that has a substrate 140, such as a printed circuit board (PCB) and, as an example, two electronic components 141 and 142 that require cooling to maintain a safe operating temperature. The heat sink 110 has a base portion 116 that, in this example, has a width $W_{HS}$ that is a substantial fraction of the width $W_{SUB}$ of the substrate 140. The heat sink 110 also has a number of fins 112 that are, in this embodiment, integral to the base portion 116. In certain embodiments (not shown), the fins 112 are separate elements thermally coupled to the base portion 116 using a method such as, for example, soldering, welding, brazing, bonding, or mechanically attachment through a compressive or interference-fit joint. In certain embodiments, the fins 112 have other configurations that provide a flow path for air to pass through the heat sink 110, as is discussed in greater detail with respect to FIG. 9.

FIG. 3B shows the heat sink 110 of FIG. 3A in an inverted orientation that in certain embodiments exposes the bottom surface 150 of base portion 116. It can be seen that two slots 152 are formed in the base portion 116, with the slots 152 oriented across the width of the heat sink 110. Thermal blocks 160 and 162 are thermally conductive elements that are thermally coupled to the base portion 116 by, for example, one of the same methods identified above for coupling the fins 112 and base portion 116. Thermal blocks 160 and 162 are sized, in certain embodiments, to be similar in size to the electrical components 141 and 142 and positioned such that the thermal blocks 160, 162 will be in contact with electrical components 141, 142 when the heat sink 110 is coupled to the motherboard 10. In certain embodiments, one thermal block (not shown) is sized and positioned to contact both electrical components 141, 142.

FIG. 3C is an exploded view of the heat sink 110 of FIG. 6B. It can be seen that slots 152 are formed in the base portion 116 of the heat sink 110. A heat pipe 170 is, when assembled, located in each slot 152 and thermally coupled to the base portion 116 through, for example, thermally conductive adhesive, an interference fit between the heat pipes 170 and the slots 152, or solder. In certain embodiments, the slot depth is selected such that the heat pipes 170 are flush with the bottom surface 150 of the heat sink 110. In the embodiment of FIGS. 3B and 3C, the thermal blocks 160, 162 are in contact with the flush-mounted heat pipes 170. In certain embodiments, additional thermal coupling between the thermal blocks 160, 162 and the heat pipes 170 is provided with, for example, a thermally conductive adhesive (not shown) under the thermal blocks 160, 162 that fills in the gaps around the heat pipes 170 in the slots 152.

In the disclosed embodiment, the heat pipes 170 serve to spread the heat from the electrical components 141, 142 across the width of the heat sink so as to increase the temperature differential between the fins 112 at the ends of the heat sink 110 and the air passing over those fins 112. Without the heat pipes 170, the fins 112 that are directly over the electrical components 141, 142 would tend to be hotter than the other fins 112 as the heat must be conducted further to the other fins 112. This temperature gradient across the fins 112 decreases the overall heat transfer from the heat sink 110 to the air, as the smaller temperature differential between the cooler more distant fins 112 and the air reduces the effectiveness of the more distant fins 112. By spreading the heat more evenly across the heat sink 110, the entire width of the heat sink is more effectively coupled to the air.

Figure 4:
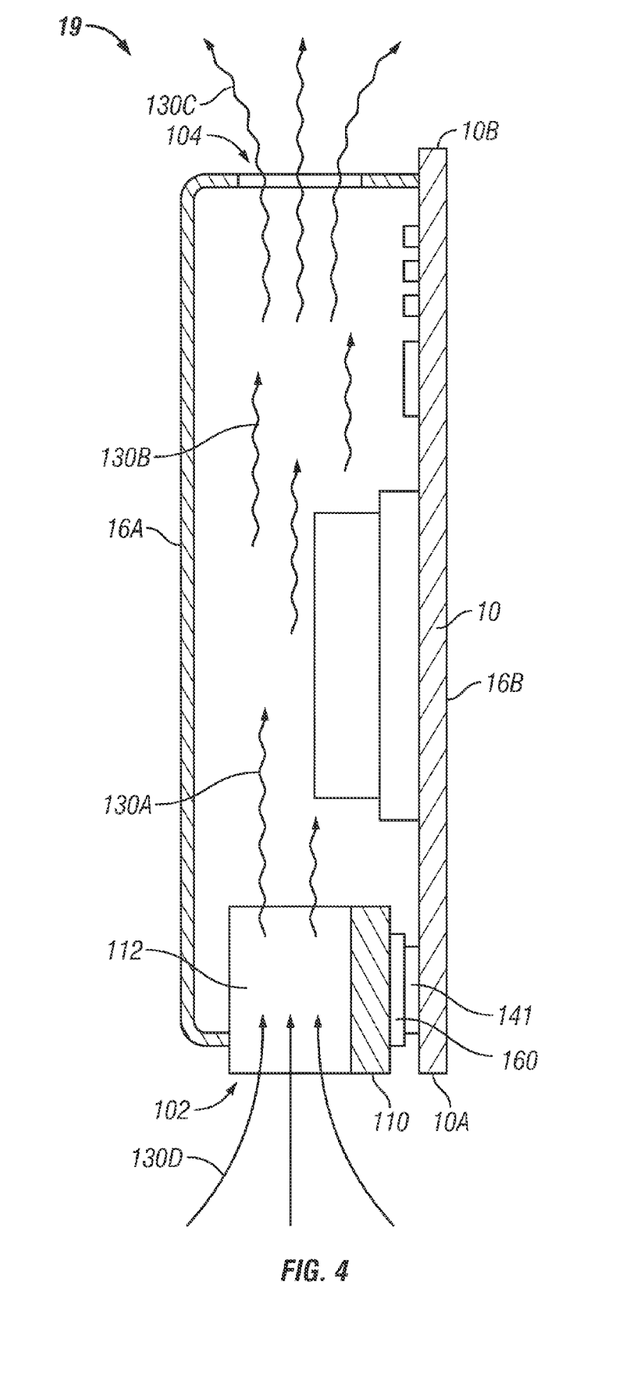
FIG. 4 is a cross-section of an assembled electronics enclosure showing the air circulation according to certain aspects of this disclosure.

FIG. 4 is a cross-section of an assembled electronics assembly 19 showing the air circulation according to certain aspects of this disclosure. In this embodiment, the motherboard 10 is oriented vertically with the trailing edge 10B located above leading edge 10A. In certain orientations, the motherboard 10 is oriented at an angle less than vertical while maintaining the trailing edge 10B above the leading edge 10A. In this embodiment, a heat sink 110 is coupled to the motherboard 10 proximate to the leading edge 10A with thermal block 160 in thermal contact with at least electrical component 141. A conductive cover 16A is coupled to the motherboard 10 with opening 102 located around the heat sink 110 and a second opening 104 located on the opposite side of the conductive cover 16A.

As heat is conducted from the electronic component 141 into the heat sink 110, the temperature of the fins 112 will rise above the ambient air temperature. Air adjacent to the heat sink 110, and especially air between the fins 112, will be heated by contact with the fins 112 and begin to rise, as indicated by arrows 130A. While initially there may be some recirculation within the interior of the conductive cover 16A as the heated air continues to rise as indicated by arrows 130B, when the heated air reaches the opening 104, the heated air will follow arrows 130C and escape through the opening 104. As this happens, cooler ambient air will enter the lower opening 102 as indicated by arrows 130D. The open passages through heat sink 110 are the only paths through opening 102 and, therefore, the ambient incoming air is immediately in contact with the heated fins 122 which will warm this new air. Once this system reaches equilibrium, there will be a continuous flow of air through the electronics assembly 19 following arrows 130D-130A-130B-130C. The gap between the fins, in this embodiment, must be large enough that the air flow does not choke at the velocities achieved in steady state.

Locating the heat sink 110 at the inlet opening 102 for the cooling air produces the maximum 'chimney' effect from the rising hot air and puts the coolest air in contact with the fins 112 of the heat sink 110, thereby maximizing the heat transferred from the fins 112 to the air. As the heat sink 110 is configured to provide the EMI shielding over that portion of the exterior, as is discussed further with respect to FIGS. 5-8, no additional EMI shielding is required over the air flow path, thereby reducing the flow resistance along the path of the cooling air.

As an example, testing of a motherboard 10 having an Intel® Atom™ D510 dual core processor 12 with a heat sink 110 and conductive enclosure 16 as described herein showed a 20° C. rise of junction temperature above ambient at a 100% duty cycle of the processor.

While the maximum chimney effect is produced with a vertical orientation of the motherboard 10, or other planar substrate for an electronics assembly, this same technique will be effective at angles away from the vertical. Enclosures tested at angles of up to 15 degrees from vertical showed good performance. As long as the outlet 104 is above the inlet 102, the air warmed by the fins 112 will rise internal to the electronics assembly 19 and draw air in through the fins 112, although the rate of air flow will be reduced as the angle from vertical increases.

Figure 5:
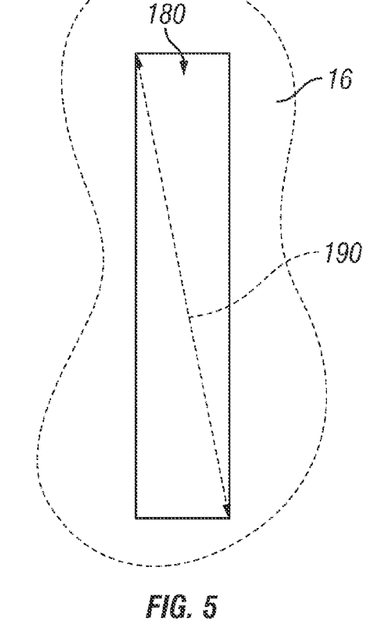
FIGS. 5-7 are views of cross-sectional openings and the maximum linear length within the opening according to certain aspects of this disclosure.
Figure 6:
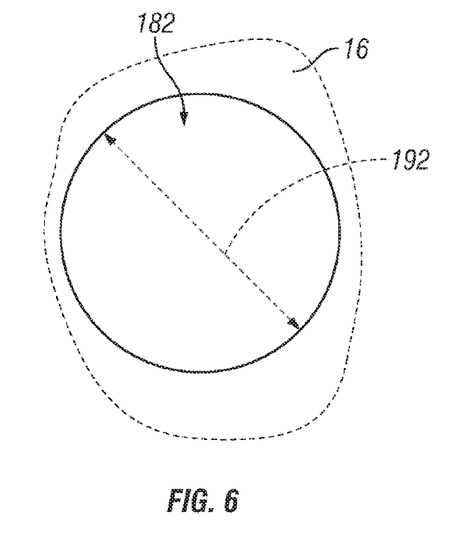
Figure 7:
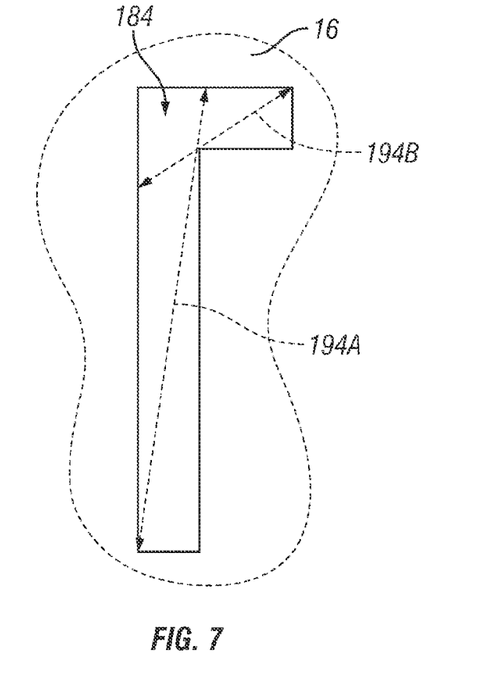

FIGS. 5-7 are views of cross-sectional openings 180, 182, and 184 and the maximum linear length 190, 192, and 194A within the opening according to certain aspects of this disclosure. Holes through conductive materials will block a range of frequencies of electromagnetic radiation up to the point where the wavelength of the electromagnetic wave is smaller than the maximum linear length of the opening. For the rectangular hole 180 in the conductive enclosure 16 (only a portion of which is depicted) shown in FIG. 5, this maximum linear length is the diagonal 190. For the example circular hole 182 in the conductive enclosure 16 shown in FIG. 6, this is the diameter 192. Irregular holes are more complex. For the example L-shaped hole 184 in the conductive enclosure 16 shown in FIG. 7, the largest linear length is line 194A from a lower corner past the inner corner of the "L" shape to the opposite wall. A candidate length 194B from the corner on the other leg is seen to be shorter than length 194A.

Figure 8:
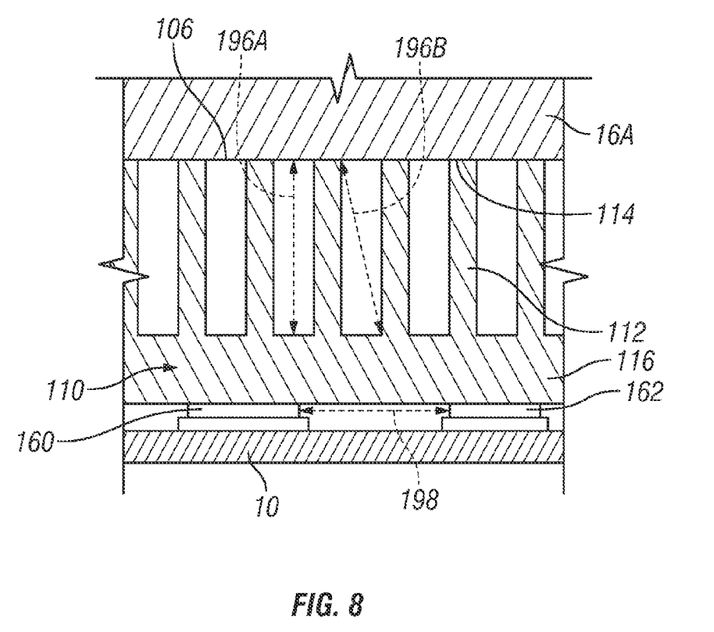
FIG. 8 is an enlarged view of a portion of the electronics enclosure of FIG. 2B according to certain aspects of this disclosure.

FIG. 8 is an enlarged view of a portion of the electronics enclosure of FIG. 2B according to certain aspects of this disclosure. Looking at the central portion of opening 102, it can be seen that the contact between the edge 106 of conductive cover 16A and the tops 114 of fins 112 leaves separate rectangular openings that, in this embodiment, are uniform in width and height. Each opening has a height 196A and a diagonal length 196B. As shown in FIG. 5, the diagonal length 196B is the maximum linear length of the openings between the fins 112.

The cutoff frequency that is blocked by an opening is approximately equal to the frequency associated with a wavelength that is twice the maximum linear length of the opening, i.e. the maximum linear length must be less than one-half wavelength. For the example of a circular hole, the hole becomes resonant with the electromagnetic wave at a half-wavelength and exhibits a shielding increase of 20 dB per decade at frequencies below the resonant frequency. The higher the range of frequencies to be blocked, the smaller the opening. The upper frequency limit of 40 GHz used in the FCC regulations has a wavelength of approximately 7.5 mm (0.29 inches) requiring openings to have a maximum linear length of less than approximately 3.8 mm, while filtering up to only 1 GHz requires openings to be smaller than 150 mm, 40 times larger. The shielding required at each frequency is dependent upon the spectral characteristics of the EMI radiator being shielded, and many devices have spikes at frequencies well below 40 GHz, such that the enclosed device may comply with the FCC regulations while having a conductive enclosure that provides effective shielding up to a frequency that is less than the 40 GHz limit.

As can be seen in FIG. 8, there are other clear passages within opening 102 besides the gaps between the fins 112. The length 198 between the thermal blocks 160, 162 may be larger than the fin height 196A. If the tops 114 of the fins 112 are not conductively coupled to the edge 106 of the conductive enclosure 16, then a nonconductive linear length may exist along the tops 114 of the fins 112 (not shown). In certain embodiments, the edge 106 is conductively attached to each top 114 such that the maximum linear length is the center-to-center spacing of the fins 112. In certain embodiments, the edge 106 is conductively coupled to the top 114 of every other fin 112, doubling this maximum linear length along the top of the heat sink 110. In certain other embodiments, the case 106 is conductively coupled only to the tops 114 of fins 112 that are separated by less than the linear distance equal to the desired cutoff frequency.

Figure 9:
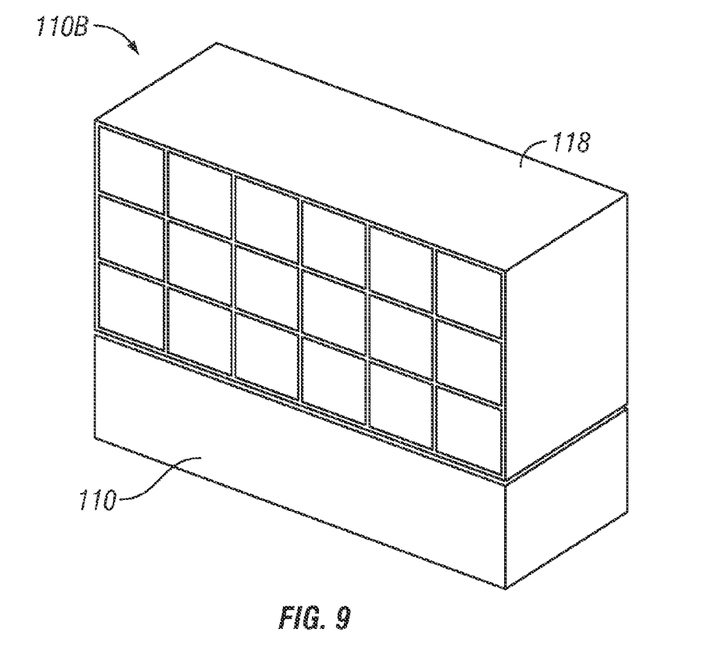
FIG. 9 is a view of another embodiment of a heat sink according to certain aspects of this disclosure.

FIG. 9 is a view of another embodiment of a heat sink 110B according to certain aspects of this disclosure. In certain embodiments, the base portion 110 is thermally coupled to a box 118 that includes a rectangular arrangement of passages formed by intersecting sheets of conductive material, for example aluminum. As each passage is open at the near end (visible) and the far end (not visible in FIG. 9), cooling air can pass through the box 118 in a manner similar to passing through the fins 112 of FIG. 4. An arrangement of this type may be more suitable than fins for higher frequencies or for other types of mechanical filtering, such as debris, as the passages are more square in the aspect ratio of the opening.

Figure 10:
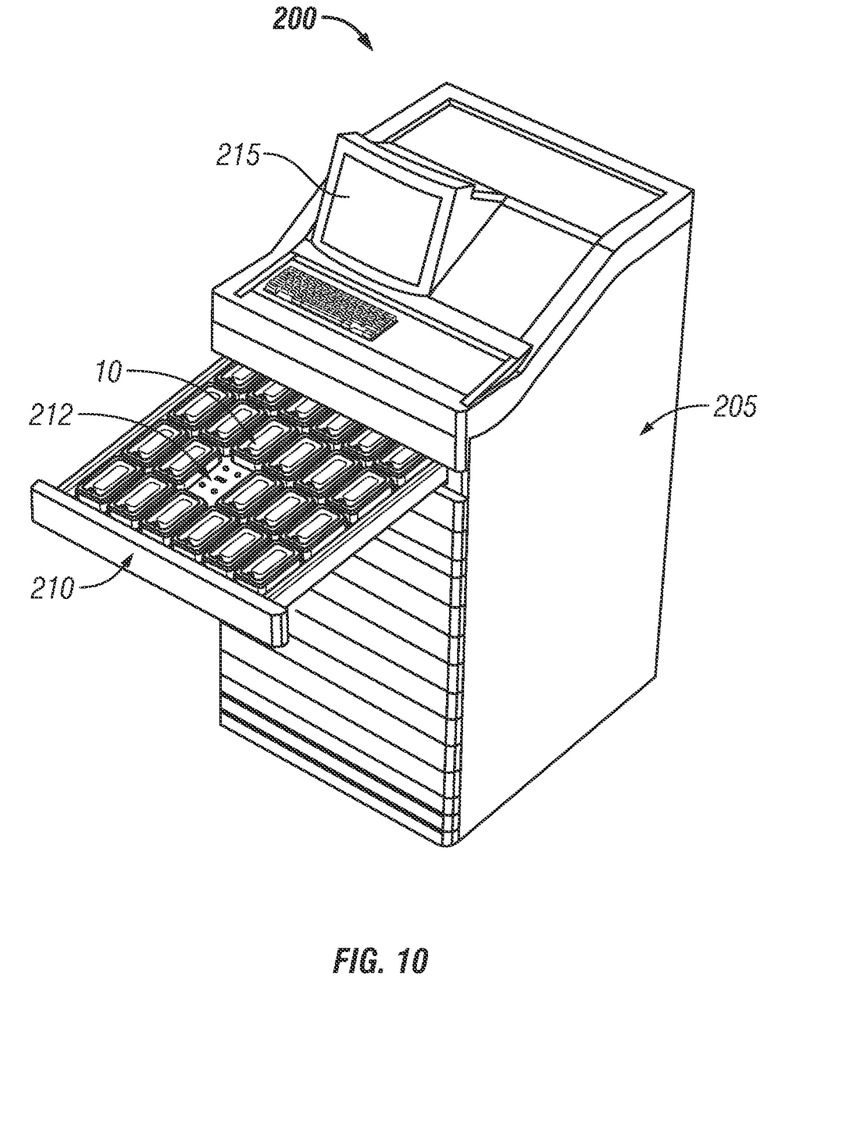
FIG. 10 is a perspective view of an ADM according to certain aspects of this disclosure.

FIG. 10 is a perspective view of an ADM 200 according to certain aspects of this disclosure. The ADM includes a cabinet 205 and a plurality of drawers 210 containing medications and medical supplies. In the illustrated embodiment of FIG. 10, at least one drawer is configured to accept removable secure storage containers 220 in locations 212. In certain embodiments, the electronics assembly 19 (not visible) is disposed behind the display 215 with the second opening 104 (not visible) located at the top of the display 215 and the first opening 102 (not visible) located at the base of the display 215 and open to the internal space under the display 215.

The concepts disclosed herein provide a method of passively cooling electronics while reducing EMI emissions from the electronics. The method includes the steps of attaching a heat sink with a base portion to an electronics assembly having at least one electronic component that requires cooling such that the base portion is thermally coupled to the at least one electronic component, and attaching a conductive enclosure to the electronics assembly so as to form an enclosed volume around the electronics assembly with a first opening fitted around the heat sink and at least one second opening, wherein all non-conductive passages from the enclosed volume to the external environment have at least one cross-sectional opening with a continuous conductive perimeter with a maximum linear length within the opening of less than one quarter wavelength of a determined maximum shielding frequency thereby reducing the EMI radiated through non-conductive passages in the conductive enclosure. When operating the electronics, at least some of the heat generated by at least some of the electronic components passes into the heat sink, whereupon at least some of the heat in the heat sink passes into the air proximate to the heat sink, whereupon the heated air passes out of the second opening thereby drawing ambient air into the enclosed volume through the first opening thereby cooling the at least one electronic component.

The disclosed electronics enclosure cools electronic components and assemblies that are disposed within the enclosure while also providing EMI shielding around the electronic components and assemblies. The electronics enclosure includes a heat sink configured to passively cool the heat-generating electronic components and a conductive enclosure configured to provide EMI shielding. By locating the heat sink at an inlet opening of the conductive enclosure and providing an outlet opening above the inlet opening, the air that is heated by the heat sink rises within the conductive enclosure and passes through the outlet opening, thereby drawing cool ambient air in through the inlet opening and into immediate contact with the heat sink. The heat sink is configured to also provide EMI shielding over the inlet opening. The electronics enclosure is coupled to the heat sink around the inlet opening and otherwise configured such that there are no gaps in the EMI shielding over the determined frequency range.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. An electronics enclosure for providing passive cooling of electronic components while reducing electromagnetic interference (EMI) emissions, the electronics enclosure comprising:
   an electronics assembly comprising a planar substrate and at least one electronic component, the planar substrate including a conductive strip around a portion of a periphery of an upper surface of the planar substrate;
   a heat sink coupled to the electronics assembly, the heat sink comprising a base portion configured to thermally couple to the at least one electronic component when the heat sink is coupled to the electronic assembly; and
   a conductive enclosure forming an enclosed volume around the electronics assembly, the enclosure comprising a first opening configured to fit around the heat sink, at least one second opening formed in the conductive enclosure spaced from the first opening, and a flange configured to mate with the conductive strip when the conductive enclosure is coupled with the planar substrate;
   wherein all non-conductive passages from the volume to the external environment have at least one cross-sectional opening having a continuous conductive perimeter with a maximum linear length within the opening of less than one quarter a wavelength of a determined maximum shielding frequency.

2. The electronics enclosure of claim 1, wherein the determined maximum shielding frequency is greater than 1 GHz.

3. The electronics enclosure of claim 1, wherein the heat sink further comprises a heat dissipation structure thermally coupled to the base portion.

4. The electronics enclosure of claim 3, wherein channels through the heat dissipation structure have widths that are large enough to avoid choked flow from natural convection.

5. The electronics enclosure of claim 4, wherein the heat dissipation structure comprises a plurality of planar fins that are separated by a distance large enough to avoid choked flow from natural convection.

6. The electronics enclosure of claim 5, wherein:
the fins are arranged in a row with an end fin at each end of the row;
each fin has a top; and
the first opening of the enclosure has an edge that is electrically coupled to the base portion and the outside surfaces of the end fins and to at least one of the tops of the fins at points separated by less than one quarter wavelength of the determined maximum shielding frequency.

7. The electronics enclosure of claim 6, wherein the fins have a height from the base portion to the top that is less than one quarter wavelength of the determined maximum shielding frequency.

8. The electronics enclosure of claim 3, wherein the heat sink further comprises at least one heat pipe that is thermally coupled to the base portion.

9. The electronics enclosure of claim 8, wherein:
the base portion of the heat sink comprises a base surface;
the at least one heat pipe is embedded in the base portion of the heat sink and flush with the base surface;
the heat sink further comprises at least one thermal block; and
the at least one thermal block is coupled to the base surface of the heat sink such that the at least one thermal block is thermally coupled to the at least one electronic component when the heat sink is coupled to the electronic assembly.

10. The electronics enclosure of claim 1, wherein:
the electronics assembly further comprising the at least one component coupled to the planar substrate, the substrate having a forward edge and a trailing edge; and
the heat sink is coupled to the electronics assembly proximate to one of the forward and trailing edges of the planar substrate.

11. The electronics enclosure of claim 10, wherein the at least one second opening is proximate to the other of the forward and trailing edges of the substrate.

12. The electronics enclosure of claim 11, wherein the planar substrate is oriented such that the trailing edge is above the leading edge.

13. An electronics enclosure for providing passive cooling of electronic components while reducing EMI emissions, the electronics enclosure comprising:
an electronics assembly comprising:
a planar substrate having a leading edge, a trailing edge, and a conductive strip around a portion of a periphery of an upper surface of the planar substrate; and
at least one electronic component coupled to the substrate proximate to the leading edge;
a heat sink coupled to the electronics assembly proximate to the leading edge of the substrate, the heat sink comprising:
a base portion;
at least one heat pipe thermally coupled to the base portion;
at least one thermal block thermally coupled to the base portion and configured to thermally couple to the at least one electronic component when the heat sink is coupled to the electronic assembly; and
a plurality of fins thermally coupled to the base portion; and
a conductive enclosure forming an enclosed volume around the electronics assembly, the enclosure comprising a first opening configured to fit around the heat sink, at least one second opening formed in the conductive enclosure spaced from the first opening, and a bottom surface configured to mate with the conductive strip when the conductive enclosure is coupled with the planar substrate;
wherein all non-conductive passages from the volume to the external environment have at least one cross-sectional opening having a continuous conductive perimeter with a maximum linear length within the opening of less than one quarter a wavelength of a determined maximum shielding frequency.

14. The electronics enclosure of claim 13, wherein:
the fins are arranged in a row having a first fin and a last fin at each end of the row and a length from the first fin to the last fin;
the row is aligned with the leading edge of the substrate; and
the heat pipe is aligned with the row of fins.

15. The electronics enclosure of claim 14, wherein:
each fin has a top; and
the first opening of the enclosure has an edge that is electrically coupled to the base portion and the outside surfaces of the first and last fins and to at least one of the tops of the fins at points separated by less than one quarter wavelength of the determined maximum shielding frequency.

16. A method of passively cooling electronics while reducing conducted and radiated EMI emissions from the electronics, the method comprising the steps of:
attaching a heat sink with a base portion to a substrate of an electronics assembly having at least one electronic component that requires cooling and an interface connector having at least one contact with an interface impedance, the interface connector configured to mate and match impedances with a docking connector having at least one contact with an interface impedance thereby reducing the EMI radiated from conductors connected to the contacts of the docking connector, such that the base portion is thermally coupled to the at least one electronic component; and
attaching a conductive enclosure to the electronics assembly so as to form an enclosed volume around the electronics assembly with a first opening fitted around the heat sink, at least one second opening formed in the conductive enclosure spaced from the first opening, and a bottom surface configured to mate with a conductive strip when the conductive enclosure is coupled with the substrate, the conductive strip located around a portion of a periphery of an upper surface of the substrate,
wherein all non-conductive passages from the enclosed volume to the external environment have at least one cross-sectional opening with a continuous conductive perimeter with a maximum linear length within the opening of less than one quarter a wavelength of a determined maximum shielding frequency thereby reducing the EMI radiated through non-conductive passages in the conductive enclosure.

17. An electronics enclosure for providing passive cooling of electronic components, the electronics enclosure comprising:
   an enclosure forming a volume having a first opening, the enclosure comprising a bottom surface;
   an electronics assembly disposed within the volume, the electronics assembly comprising a motherboard and at least one electronic component the motherboard having a conductive strip around a portion of a periphery of an upper surface of the motherboard, the conductive strip configured to mate with the bottom surface of the enclosure when the enclosure is coupled with the motherboard; and
   a heat sink coupled to the at least one electronic component, the heat sink having a width, the heat sink comprising at least one heat pipe configured to transfer heat across the width of the heat sink;
   wherein the heat sink is disposed proximate to the first opening such that air that passes through the first opening will tend to pass through the heat sink;
   wherein the enclosure comprises a conducting surface and all non-conductive passages from the volume to the external environment have at least one cross-sectional opening having a continuous conductive perimeter with a maximum linear length within the opening of less than one quarter a wavelength of a determined maximum shielding frequency.

18. The enclosure of claim 17, wherein the heat sink further comprises a plurality of fins configured such that air that passes through the first opening will tend to pass between the fins.

19. The enclosure of claim 17, wherein the heat pipe comprises a hollow cylinder and the cylinder is enclosed on at least three sides by the heat sink.

* * * * *